(12) United States Patent
Koppes et al.

(10) Patent No.: US 6,833,454 B1
(45) Date of Patent: Dec. 21, 2004

(54) CHEMICAL COMPOUNDS CONTAINING BIS (TRIAZOLO)TRIAZINE STRUCTURES AND METHODS THEREOF

(75) Inventors: William M. Koppes, Adelphi, MD (US); Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/342,657

(22) Filed: Jan. 15, 2003

(51) Int. Cl.⁷ .................... C07D 487/04; C07D 487/14
(52) U.S. Cl. ........................... 544/198; 544/209
(58) Field of Search .................................. 544/198, 209

(56) References Cited

U.S. PATENT DOCUMENTS

| | | | |
|---|---|---|---|
| 3,312,699 A | 4/1967 | Gladych et al. | 260/249.8 |
| 4,312,988 A | 1/1982 | Jacobs, III et al. | 544/196 |
| 4,316,022 A | 2/1982 | Hajos et al. | 544/184 |
| 5,164,496 A | 11/1992 | Hochstetter | 540/544 |
| 5,677,309 A | 10/1997 | Chen et al. | 514/267 |
| 5,785,720 A | 7/1998 | Eichenberger et al. | 8/567 |

*Primary Examiner*—Venkataraman Balasubramanian
(74) *Attorney, Agent, or Firm*—Mark Homer

(57) ABSTRACT

Chemical compounds having a bis(triazolo)triazine structure, including complexes and salts thereof, may be useful in either an intermediate or final product.

17 Claims, No Drawings

CHEMICAL COMPOUNDS CONTAINING BIS (TRIAZOLO)TRIAZINE STRUCTURES AND METHODS THEREOF

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to novel fused ring structures useful for providing a platform for novel explosive and pyrotechnic compounds, particularly high nitrogen content, low carbon content energetic compounds, dyes, pharmaceutical and other compositions. The present invention includes chemical compounds having a bis(triazolo)triazine structure, either as an intermediate or final product, including complexes and salts thereof, and other such chemical structures as detailed herein.

2. Brief Description of the Related Art

No methods are known for the preparation of chemical compounds having bis(triazolo)triazine structures, particularly bis(aminotriazolo)-substituted-triazine structures such as bis(aminotriazolo)aminotriazine structures.

SUMMARY OF THE INVENTION

The present invention includes chemical compounds having a bis(triazolo)triazine structure, particularly bis(aminotriazolo)-substituted-triazine such as bis(aminotriazolo)aminotriazine, either as an intermediate or final product, including complexes and salts thereof.

The present invention also includes a method for producing chemical compounds having a bis(triazolo)triazine structure, including for example bis(triazolo)triazine hydrochloric salt such as bis(aminotriazolo)aminotriazine hydrochloric salt and bis(aminotriazolo)aminotriazines. These materials can be used as intermediates or final product of energetic ingredients in propellants, explosives, pyrotechnics and gas generators, or a variety of other organic compounds, including pharmaceuticals and azo dyes.

DETAILED DESCRIPTION OF THE INVENTION

The present invention includes chemical compounds having a bis(triazolo)triazine structure. Preferably the bis(triazolo)triazine structure comprises the formula:

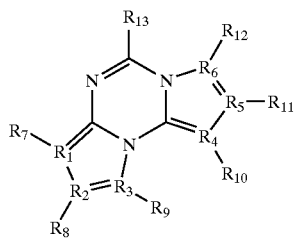

wherein $R_1$, $R_2$ and $R_3$ independently comprise either a nitrogen or carbon atom and together comprise two nitrogen atoms and one carbon atom, and wherein when $R_3$ comprises a nitrogen atom then $R_2$ comprises a carbon atom; $R_4$, $R_5$ and $R_6$ independently comprise either a nitrogen or carbon atom and together comprise two nitrogen atoms and one carbon atom, and wherein when $R_6$ comprises a nitrogen atom then $R_5$ comprises a carbon atom; $R_7$, $R_8$, $R_9$, $R_{10}$, $R_{11}$, and $R_{12}$, independently, are present only connected to a carbon atom, comprise $-NH_2$, and $R_{13}$ comprises an electron donating group selected from the group consisting of lower alkylamino, diloweralkylamino, amino, halo, aryl, lower alkoxy, lower aralkoxy, aryloxy, mercapto, and lower alkylthio.

Because of the reactive properties of the amino units on the triazolo rings of the bis(aminotriazolo)-substituted-triazine, when used as an intermediate the bis(aminotriazolo)-substituted-triazine is useful in deriving compounds for ingredients in propellants, explosives, pyrotechnics, gas generators, ultraviolet absorbers, pharmaceuticals, colorants and dyes, etc. as later described.

As used herein, an "electron donating group" designates a group that will release or donate electrons more than hydrogen would if it occupied the same position in the molecule. See J. March, Advanced Organic Chemistry, $3^{rd}$ Ed., John Wiley & Sons p. 238 (1985). These types of groups are well known in the art. Examples include lower alkylamino, diloweralkylamino, amino, halo, aryl, lower alkoxy, lower aralkoxy, aryloxy, mercapto, lower alkylthio, and the like, including for example, $O^-$, $-COO^-$, $-OR_\alpha$, $-CR_\alpha R_\beta R_\gamma$, $-OCOR_\alpha$, $-NR_\alpha R_\beta$, and $SR_\alpha$, where $R_\alpha$, $R_\beta$, and $R_\gamma$, groups are independently H or an alkyl group, such as methyl, ethyl, propyl, isopropyl, tert-butyl, isobutyl, and the like. The preferred electron donating groups are amino, hydroxy, lower alkoxy, lower alkylamino and diloweralkylamino. The most preferred electron donating group is amino. Lower used herein denotes straight-chain and branched hydrocarbon moieties containing from 1 to 8 carbon atoms. Electron donating groups include atoms that can stabilize the developing positive charge in a ring closure by Mesomeric Effect, such as methoxy groups. Preferably, the electron donating group comprises either $-OCH_3$ or $-NH_2$. Most preferably, the electron donating group comprises $-NH_2$.

Some preferred embodiments of the present invention provides a method for forming bis(aminotriazolo)-substituted-triazines of several isomeric structures, preferably bis(aminotriazolo)aminotriazines. Non-limiting representative bis(aminotriazolo)-substituted-triazine structures of the present invention include the following variations (Formulas A–C):

Formula A

-continued

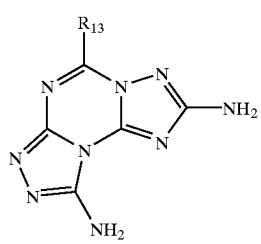

Formula B

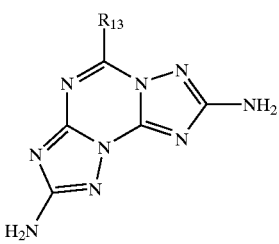

Formula C

Most preferably, a number of isomeric structures for bis(aminotriazolo)aminotriazines are possible based on the position of the aminotriazolo group on the triazine ring, in addition to the arrangement of N and C atoms within the aminotriazolo group itself. Bis(aminotriazolo)aminotriazine of Structure I, below, is initially formed via ring closure reactions of hydrazino groups [on 2-amino-4,6-dihydrazino-1,3,5-triazine (IV)] with cyanogen bromide (see Scheme 1 below). Subsequent rearrangements of Structure I provide either Structures II and/or Structure III, below, through a Dimroth Rearrangement Representative examples of these structures are shown below (Structures I, II and III).

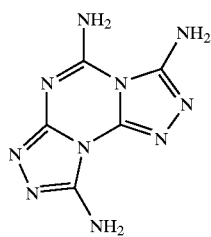

Structure I

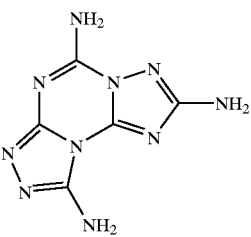

Structure II

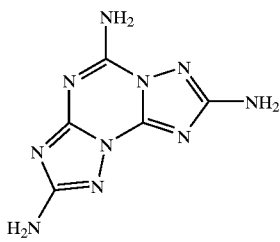

Structure III

The chemical compound having a bis(triazolo)triazine structure of the present invention may be produced by dissolving the 2-substituted-4,6-dihydrazino-1,3,5-triazine (with the 2-substituted component of the 2-substituted-4,6-dihydrazino-1,3,5-triazine comprising an electron donating group), preferably 2-amino-4,6-dihydrazino-1,3,5-triazine, with an acid. This step is preferably carried out at room temperature with an acid that is of sufficient strength to dissolve the 2-amino-4,6-dihydrazino-1,3,5-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid.

In an additional step the dissolved 2-amino-4,6-dihydrazino-1,3,5-triazine is mixed with a reagent of the formula RCN, wherein R comprises a leaving group. This reaction provides two amino triazole rings on the product directly. Ring closure occurs at both hydrazine nitrogen atom groups, forming two triazole rings on the 2-substituted-4,6-dihydrazino-1,3,5-triazine, with a non-neutralized product of a bis(aminotriazolo)-substituted-triazine salt and neutralized product of a bis(aminotriazolo)-substituted-triazine compound. The general formulas for the process are set forth below (showing the preferred embodiment of an electron donating group of the 2-substituted component of $-NH_2$). This preferred embodiment of the process involves ring closure of a 2-amino-4,6-dihydrazino-1,3,5-triazine with an acid, as previously described such as HCl and a chemical such as BrCN, and then neutralizing the acid with an appropriate compound such as $K_2CO_3$. Ring closure occurs at both hydrazine nitrogen atom groups, forming two triazole rings on the 2-amino-4,6-dihydrazino-1,3,5-triazine, with a non-neutralized product of bis(aminotriazolo)aminotriazine salt and neutralized product of bis(aminotriazolo)aminotriazine compound. A leaving group, as used in this application, is a group that can be displaced to give ring closure; that is, produces the amino triazole rings. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. The crystals may be removed by any known method as understood by one skilled in the art, such as filtration, and can then be washed and dried in order to obtain the final acid salt product.

Additional steps of removing acid salt crystals and neutralizing the acid salt crystals may be used as desired. The present invention also includes a process to take the bis(triazolo)triazine, preferably bis(aminotriazolo)aminotriazine, acid salt synthesized above, and neutralize the acid salt crystals to obtain a final product of a bis(triazolo)triazine. This process involves the steps described above as well as the following steps.

First, the acid salt crystals are removed from the solution synthesized above. Then, the acid salt crystals are neutralized by mixing them with a substance more basic than the bis(triazolo)triazine. This step results in the removal of the acid from the above reaction and provides for a final product of a bis(triazolo)triazine. The substance used in this final step may be selected by one skilled in the art based upon the basicity of the substance versus the basicity of the bis(triazolo)triazine, which may vary with differing substituents and may be readily determined by those skilled in the art. Some examples of the basic substance are potassium carbonate, potassium acetate, sodium bicarbonate, and sodium hydroxide. One preferred substance is potassium carbonate. It is also preferred that the reaction take place in solution, so preferably, water or some other solvent may be added to the salt. The general formulas for the process are set forth below in Scheme 1:

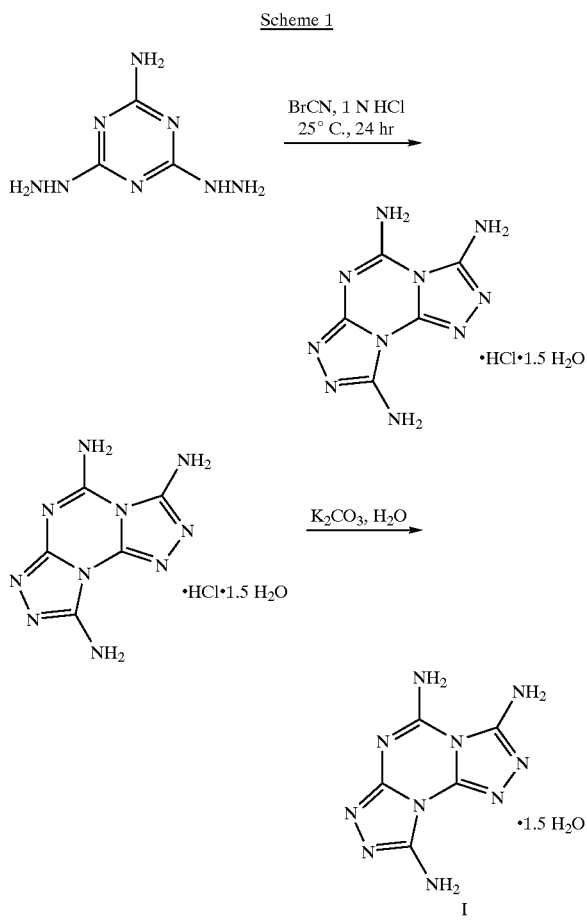

EXAMPLE 1A

Preparation of bis(aminotriazolo)aminotriazines (Hydrochloric Salt)

To 90 mL of 1 N hydrochloric acid stirred at 25° C. was added 7.7 g (0.049 mole) of 2-amino-4,6-dihydrazino-1,3, 5-triazine (prepared as described in Examples 3A and 3B). The mixture was stirred for 10 minutes at which time essentially all material had dissolved (very small amounts of undissolved material were present at this point and were removed by filtration). Cyanogen bromide (15.1 g, 0.142 mole) was added at one time and the mixture was stirred in the stoppered flask until all material was in solution. Stirring was discontinued and the mixture was allowed to stand for 24 hours to produce a crystalline precipitate. The crystals were removed by filtration and washed with cold distilled water. The product was air dried and then dried in a vacuum desiccator over Drierite to give 6.37 g of white crystals. The filtrate gave an additional amount of white crystals (2.44 g) after standing for several days. Total yield: 8.81 g [67% of the theoretical yield of hydrochloric salt (1.5H$_2$O)]. Melting point: >300° C. $^1$H NMR (DMSO-d$_6$): merged broad peaks at 6.7 and 7.1; slightly broadened singlets at 8.68 and 9.34. Anal. Calcd for C$_5$H$_6$N$_{10}$ (HCl) (1.5H$_2$O): C, 22.27; H, 3.74; N, 51.94; Cl, 13.15. Found: C, 22.12; H, 3.16; N, 51.38; total halogens as Cl, 14.17.

EXAMPLE 1B

Preparation of bis(aminotriazolo)aminotriazines (Neutralized Product)

The product of Example 1A (the hydrochloric salt) (1.5H$_2$O) (6.1 g, 0.0226 mole) was stirred vigorously in 150 mL of distilled water at 25° C. Potassium carbonate (4.0 g, 0.029 mole) was added and vigorous stirring was continued for 30 minutes before the mixture was filtered and the insoluble white solid was washed well with cold distilled water (250 mL). The neutralized product was dried in a vacuum desiccator to give 4.47 g (85%) of bis (aminotriazolo)-aminotriazine (1.5H$_2$O). The product acquires a light purple tint due to slow air oxidation on the exposed solid surface. Melting point: >300° C. $^1$H NMR (DMSO-d$_6$): 5.90 (s, 2H); 6.34 (s, 2H); 7.63 (broad s, 2H). $^{13}$C NMR (DMSO-d$_6$): 143.8, 144.0, 145.5, 147.3, 162.6. Anal. Calcd for C$_5$H$_6$N$_{10}$ (1.5H$_2$O): C, 25.75; H, 3.89; N, 60.07. Found: C, 25.77; H, 3.90; N, 59.36. A small sample of neutralized product was dissolved in a minimum amount of DMSO at 25° C. The solution was allowed to stand in an open beaker in the hood to slowly grow crystals. X-ray crystal structure analysis showed the crystals were the Dimroth rearranged product (structure II).

EXAMPLE 2

Preparation of bis(aminotriazolo)aminotriazines (Dimroth Rearrangement at 150–155° C.)

A sample (0.61 g) of the neutralized product from Example 1 was stirred in DMSO (9.8 mL) at 150–155° C. for two hours (all material dissolves around 90° C., but a solid precipitates after a short time at 150–155° C.). The reaction mixture was cooled to 25° C. before the insoluble solid (0.09 g, first crop) was removed by filtration and washed with a small amount of DMSO and water. Water (30 mL) was added to the filtrate to precipitate a second crop of product (0.33 g). TLC and NMR analyses showed the second crop was mainly the same product as the first crop, but the second crop contained small amounts of starting material and unidentified impurities. Melting point: >300° C. $^1$H NMR (DMSO-d$_6$): 6.07 (broad s with small shoulder, 4H); 9.26 (broad s, 2H). $^{13}$C NMR (DMSO-d$_6$). 138.4, 155.3, 166.6.

Preparation of Precursor

The present invention also provides a method for producing high-purity 2-amino-4,6-dihydrazino-1,3,5-triazine via 2-amino-4,6-dimethoxy-1,3,5-triazine (formed from 2,4,6-trimethoxy-1,3,5-triazine), shown in Scheme 2, below. Reported melting points in the literature for 2-amino-4,6-dihydrazino-1,3,5-triazine are significantly lower than the 2-amino-4,6-dihydrazino-1,3,5-triazine material resulting from the method described herein. The availability of high-purity 2-amino-4,6-dihydrazino-1,3,5-triazine greatly facilitates the production and isolation of pure bis(aminotriazolo) aminotriazines.

The following examples (Examples 3A–3B) are preparations of the 2-amino-4,6-dimethoxy-1,3,5-triazine from 2,4, 6-trimethoxy-1,3,5-triazine (Example 3A), and 2-amino-4, 6-dihydrazino-1,3,5-triazine from 2-amino-4,6-dimethoxy-1,3,5-triazine (Example 3B), with the reaction shown in Scheme 2, below.

EXAMPLE 3A

Preparation of 2-amino-4,6-dimethoxy-1,3,5-triazine precursor

A mixture of 10.1 g (0.059 mole) of 2,4,6-trimethoxy-1, 3,5-triazine and water (100 mL) was stirred at 25° C. while 110 mL of 28% aqueous ammonia was added. The mixture was held at 48–51° C. for two hours before it was cooled to 25° C. and the insoluble white crystals were removed. The product was washed with water and dried to give 7.84 g (86%), mp 218–221° C. $^1$H NMR (DMSO-d): 3.81 (s, 6H); 7.38 (s, 2H). $^{13}$C NMR (DMSO-d$_6$): 53.9, 169.0, 171.9.

EXAMPLE 3B

Preparation of 2-amino-4,6-dihydrazino-1,3,5-triazine percursor

A mixture of 8.1 g (0.052 mole) of 2-amino-4,6-dimethoxy-1,3,5-triazine and water (103 mL) was stirred at 25° C. while 77 mL of hydrazine monohydrate was added. The mixture was held at 120–125° C. (slow reflux) for three hours. The mixture was cooled to 25° C. and the insoluble white crystals were removed, washed first with water and then ethanol, and dried to give 8.0 g (98%), mp 290° C., dec. NMR analysis indicated the product was very pure (no impurity peaks could be detected). $^1$H NMR (DMSO-d$_6$): 4.05 (s, 4H); 6.22 (s, 2H); 7.63 (s, 2H). $^{13}$C NMR (DMSO-4): 166.3, 167.5. It is noted that the reported melting points in the literature for 2-amino-4,6-dihydrazino-1,3,5-triazine are significantly lower than the material from the present method. For example, a recent publication in Bull. Chem. Soc. Japan, 70(3), page 671–679 (1997) reports a melting of 262° C. for 2-amino-4,6-dihydrazino-1,3,5-triazine. The methods of the present invention include production of a high-purity 2-amino-4,6-dihydrazino-1,3,5-triazine.

Scheme 2

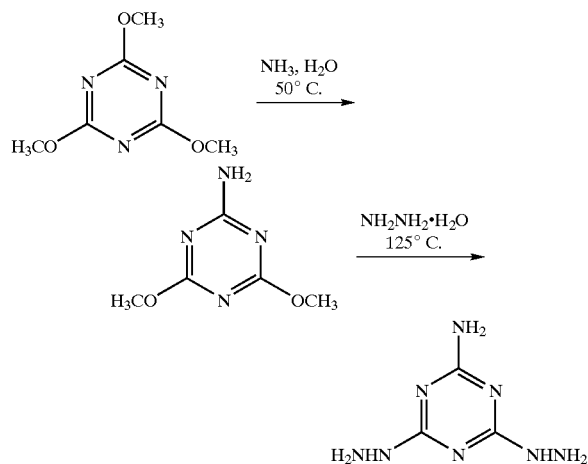

The reaction of the 2,4,6-trimethoxy-1,3,5-triazine may be accomplished with ammonia (as shown in Scheme 2) or any appropriate substituted amine, including for example, mono- or di-C$_{1-4}$ alkyl substituted amines such as methyl, ethyl, propyl, iso-propyl, butyl and iso-butyl substituted amines, mono-aryl substituted amines, aryl/C$_{1-4}$ alkyl di-substituted amines, and the like, with the resultant compound being a 2-substituted-4,6-dimethoxy-1,3,5-triazine, as appropriate for a given substituted amine with the resultant compound being readily known by one skilled in the are. Reaction of the 2-substitued-4,6-dimethoxy-1,3,5-triazine (shown in Scheme 2 as 2-amino-4,6-dimethoxy-1,3,5-triazine) may be accomplished by any appropriate hydrazine compound such as hydrazine, hydrazine monohydrate, and the like, to form a 2-substituted-4,6-dihydrazino-1,3,5-triazine (shown in Scheme 2 as 2-amino-4,6-dihydrazino-1,3,5-triazine), with the substituted component being determinable by the substituted component of the 2-substituted-4,6-dimethoxy-1,3,5-triazine.

Due to the reactive nature of the —NH$_2$ from the five-member rings, derivatives of the bis(aminotriazolo)-substitued-triazine, as described below as an intermediate, are useful in a wide range of fields, including for example, pharmaceuticals, including treating compositions, such as topical lotions including without limitation sunscreen, creams and/or therapeutic liquids, over-the-counter and/or prescription drugs, parental drugs, injectable drugs, food supplements, agricultural compositions, such as without limitation herbicides, pesticides, fungicides and/or fertilizers; ultraviolet (UV) stabilizers and ultraviolet absorbers, colorants such as dyes, pigments and other color applicants, such as without limitation paints, textile colorants and/or indicators, including liquid crystal uses and other indicators for computer display screens, explosives, pyrotechnics and gas generators, such as for use in airbags and other like functions; and/or fluids, such as functional fluids, additives and/or stabilizers, for use in machinery and/or other mechanical applications. The intermediate may be used to anchor functional groups, such as benzophenones, benzotriazoles, substituted acrylonitriles and phenol-nickel complexes for ultraviolet absorbers, use of the intermediate as an additive for a functional fluid (see e.g. U.S. Pat. No. 3,939,084 to Sullivan purporting to use a 3,5,7-Triamino-s-triazolo (4,3-a)-s-triazine as an additive (col. 14, lns. 60–61) in Table I; which is a mislabeled 3,5,7-Triamino-s-trizazolo (1,5-a)-s-triazine), or chromogens as detailed below. For example, triazoles and/or triazines are known in the fields of agriculture (see e.g., U.S. Pat. No. 5,602,075 to Benko et al., herbicides), pharmaceuticals (see e.g., U.S. Pat. No. 5,380,714 to Jones et al., U.S. Pat. No. 5,457,091 to Jaehne et al., U.S. Pat. No. 5,246,932 to Caulkett et al., U.S. Pat. No. 6,107,300 to Bakthavatchalam et al. and U.S. Pat. No. 5,489,591 to Kobayashi et al.), colorants (see e.g., U.S. Pat. Nos. 3,758,309 and 3,725,067 to Bailey et al., U.S. Pat. No. 4,236,003 to Fletcher, and U.S. Pat. No. 4,621,046 to Sato et al.), and agricultural chemicals, medicines, dyes, paints, and the like, as various resin materials, such as aminoplast molded materials and flame retarding materials (see e.g., U.S. Pat. No. 6,127,538 to Tanaka et al.; see col. 1, lns. 26–30; see also U.S. Pat. No. 5,371,218 to Cipolli et al.). The bis(triazolo)triazine intermediate is most particularly useful in energetic materials, such as explosive, pyrotechnic and/or gas generator compositions. Aminotriazine compounds have special applicability in demolitions, fireworks and airbag inflating compositions. For example, the fireworks compositions are preferably low smoke compositions have decreasing amounts of residual smoke after pyrotechnic burn that are operationally and commercially useful. The bis(triazolo)triazine compounds of the present invention, and their complexes and salts, provide a high-nitrogen content, low-carbon content energetic material as an intermediate to produce a final pyrotechnic composition, which generally further includes the addition of an oxidant to fully consume the carbon and hydrogen components of the pyrotechnic compositions during burning and one or more colorants. It is also preferred to use the bis(triazolo)triazine compounds as intermediates in colorants of a dye or pigment, such as by incorporation of an elongated conjugation sufficient to create a chromogen, preferably with a chromophore, including azo dyes, having a (—N=N—) linkage or imino dyes having a (—N=CR$_a$R$_b$—) linkage, such as (—N=CR$_a$Ar$_x$—), where R$_a$ and R$_b$ represent additional dye forming substituents, such as aryl groups, e.g., multiple and/or fused aryl groups (Ar$_x$), with representative including anthraquinones, triphenylmethanes, azines, phthalocyanines, indoles, and the like.

The foregoing summary, description, and examples of the invention are not intended to be limiting, but are only exemplary of the inventive features which are defined in the claims.

What is claimed is:

1. A compound having the formula:

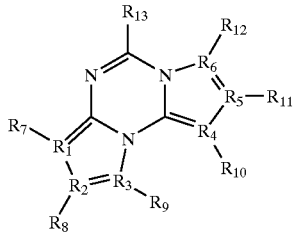

wherein $R_1$, $R_2$ and $R_3$ independently comprise either a nitrogen or carbon atom and together comprise two nitrogen atoms and one carbon atom, and wherein when $R_3$ comprises a nitrogen atom then $R_2$ comprises a carbon atom;

wherein $R_4$, $R_5$ and $R_6$ independently comprise either a nitrogen or carbon atom and together comprise two nitrogen atoms and one carbon atom, and wherein when $R_6$ comprises a nitrogen atom then $R_5$ comprises a carbon atom;

wherein $R_7$, $R_8$, $R_9$, $R_{10}$, $R_{11}$ and $R_{12}$, independently, are present only connected to a carbon atom, comprise —NH$_2$; and, wherein $R_{13}$ comprises an electron donating group selected from the group consisting of lower alkylamino, diloweralkylamino, amino, halo, aryl, lower alkoxy, lower aralkoxy, aryloxy, mercapto, and lower alkylthio.

2. The compound of claim 1, wherein $R_{13}$ is an electron donating group selected from the group consisting of a hydroxyl salt, a carboxyl salt, —OR$_\alpha$, —CR$_\alpha$R$_\beta$R$_\gamma$, —OCOR$_\alpha$, —NR$_\alpha$R$_\beta$, and SR$_\alpha$, where R$_\alpha$, R$_\beta$, and R$_\gamma$ groups are independently an alkyl group or H.

3. The compound of claim 1, wherein $R_{13}$ is an electron donating group selected from the group consisting of amino, hydroxy, lower alkoxy, lower alkylamino and diloweralkylamino.

4. The compound of claim 3, wherein $R_{13}$ is —OCH$_3$ or —NH$_2$.

5. The compound of claim 4, wherein $R_{13}$ is —NH$_2$.

6. The compound of claim 1, having the structure of:

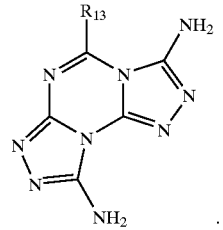

7. The compound of claim 6, wherein $R_{13}$ is —OCH$_3$ or —NH$_2$.

8. The compound of claim 7, wherein $R_{13}$ is —NH$_2$.

9. The compound of claim 1, comprising having the structure of:

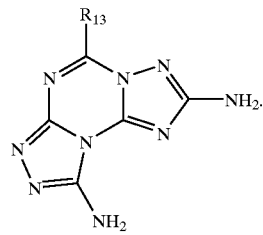

10. The compound of claim 9, wherein $R_{13}$ is —OCH$_3$ or —NH$_2$.

11. The compound of claim 10, wherein $R_{13}$ is —NH$_2$.

12. The compound of claim 1, having the structure of:

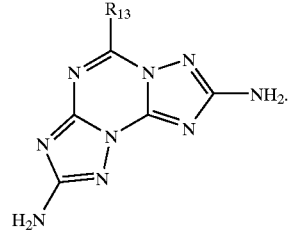

13. The compound of claim 12, wherein $R_{13}$ is —OCH$_3$ or —NH$_2$.

14. The compound of claim 13, wherein $R_{13}$ is —NH$_2$.

15. A method for producing the compound of claim 1, comprising the steps of:

dissolving a 2-substituted-4,6-dihydrazino-1,3,5-triazine with an acid; and, mixing the dissolved 2-substituted-4,6-dihydrazino-1,3,5-triazine with a reagent of the formula RCN, wherein R comprises a leaving group, wherein the 2-substituted component of the 2-substituted-4,6-dihydrazino-1,3,5-triazine comprises an electron donating group, wherein an acid salt crystal product forms, wherein the acid salt crystal product is optionally neutralized.

16. A method of forming 2-substituted-4,6-diydrazino-1,3,5-triazine, comprising the steps of:

reacting 2,4,6-trimethoxy-1,3,5-triazine with an amine, wherein such amine is selected from the group consisting of ammonia, mono-C$_{1-4}$ alkyl substituted amines, di-C$_{1-4}$ alkyl substituted amines, mono-aryl substituted amines and aryl/C$_{1-4}$ alkyl di-substituted amines, to form a 2-substituted-4,6-dimethoxy-1,3,5-triazine; and, reacting the 2-substituted-4,6-dimethoxy-1,3,5-triazine with a hydrazine to form a from 2-substituted-4,6-diydrazino-1,3,5-triazine.

17. The method of forming the compound of claim 1, comprising the step of:

forming a first compound of claim 1, wherein both triazole rings have a carbon atom adjacent to a fused nitrogen atom in the triazine ring;

optionally, placing the formed first compound in solution; and, inputting sufficient energy into the formed first compound wherein a rearrangement occurs to form at least a second compound of claim 1, wherein one or both triazole rings have a nitrogen atom adjacent to the nitrogen atom in the triazine ring.

* * * * *